United States Patent [19]

Ferrari et al.

[11] Patent Number: 4,990,794
[45] Date of Patent: Feb. 5, 1991

[54] SENSING-MEASURING DEVICE FOR CONTINUOUS DETERMINATION OF CAVITATION IN DYNAMIC PUMPS

[75] Inventors: Marco Ferrari, Campi Bisenzio; Pierluigi Nava, Florence, both of Italy

[73] Assignee: Nuovopignone-Industrie Meccaniche E Founderia, Florence, Italy

[21] Appl. No.: 482,546

[22] Filed: Feb. 21, 1990

[30] Foreign Application Priority Data

Feb. 22, 1989 [IT] Italy ............................... 19519 A/89

[51] Int. Cl.⁵ .............................................. G01N 15/06
[52] U.S. Cl. .................................. 250/573; 250/227.25
[58] Field of Search ........... 250/573, 574, 576, 227.25; 356/445, 337, 338; 417/18, 454

[56] References Cited

U.S. PATENT DOCUMENTS 4,808,092 2/1989 Funke .................................. 417/454
4,915,591 4/1990 Funke .................................. 417/18

Primary Examiner—David C. Nelms
Assistant Examiner—Stephone B. Allen
Attorney, Agent, or Firm—Morgan & Finnegan

[57] ABSTRACT

A sensing-measuring device for the continuous determination of cavitation in dynamic pumps, consisting of an optical probe mounted in proximity to the suction nozzle of the dynamic pump, said probe comprising a light emitter and an optical sensor which are positioned inclined at an angle to each other in such a manner as to perfectly center on the leading edge of the blades.

2 Claims, 1 Drawing Sheet

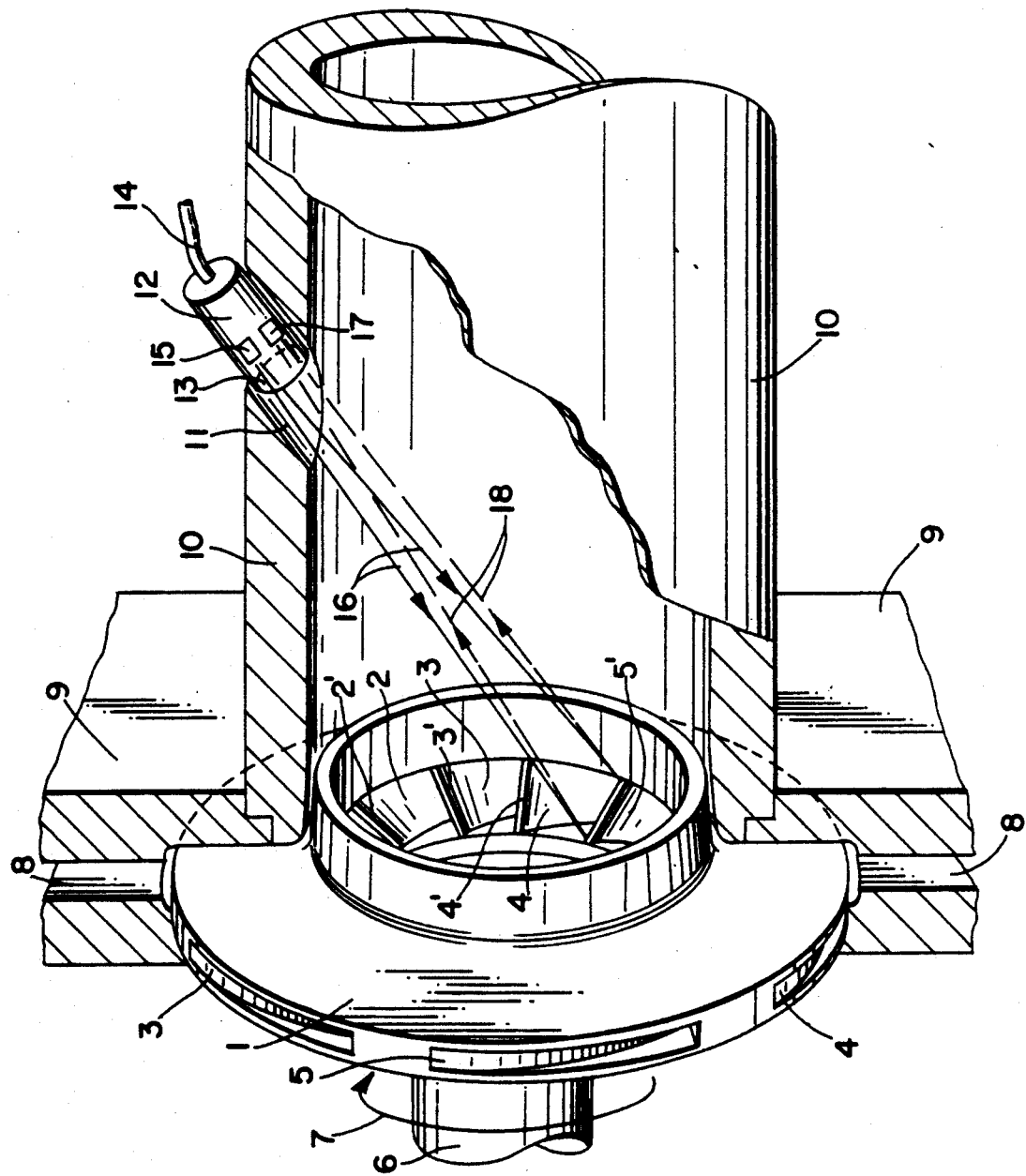

SENSING-MEASURING DEVICE FOR CONTINUOUS DETERMINATION OF CAVITATION IN DYNAMIC PUMPS

This invention relates to a simple, low-cost sensing-measuring device for the continuous determination of cavitation in dynamic pumps which not only enables the cavitation phenomenon to be sensed effectively and directly, and therefore reliably, as early as the appearance of the initial gas bubbles (incipient cavitation), but also allows the phenomenon to be measured accurately and continuously, with consequent determination of its variation with time.

It is well known that if the suction pressure is progressively reduced in a dynamic pump while keeping all other parameters constant, the evolvement of gas bubbles is observed, located initially on the leading edge of the blades (incipient cavitation). This latter phenomenon does not appreciably influence the pump performance but has a negative effect on the pump life in that the implosion of the gas bubbles causes blade corrosion and erosion. Again, if the pressure is further reduced, there is a considerable increase in the generation of gas bubbles (full cavitation) and the pump performance falls off considerably. From the aforegoing it is clear that the performance and life of a dynamic pump are negatively influenced by the cavitation phenomenon, it therefore being apparent that a system able to sense the phenomenon as soon as it occurs would be an advantage. Various systems are already known in the state of the art for sensing cavitation in dynamic pumps, and these can be substantially divided into two categories, the first of which is used only in those laboratories specifically set up to study the phenomenon, and employs stroboscopic lamps synchronized with the rotational speed of the blades, these allowing visual inspection of the blades and thus determination of when gas bubbles commence. Such a visual system has however a series of drawbacks deriving from the need for substantial modifications to the suction side of the pump, and the requirement for constant operator presence to observe the phenomenon.

The sensing systems of the second category are used industrially, where a pump has to be monitored to prevent it operating under cavitational conditions, and utilize indirect sensing of the phenomenon in the sense that secondary effects produced by the cavitation such as noise, vibration, pressure pulses etc. are sensed using suitable sensors. These systems also have drawbacks, due substantially to the fact that indirect sensing of the cavitation phenomenon is very difficult and problematic, as said secondary effects to be sensed can also be induced by many other causes which are independent of cavitation. In addition, it is very problematic if not impossible to determine the phenomenon at the incipient cavitation level, because said secondary effects such as noise and vibration arise only when cavitation is at an advanced level. In addition, the signals produced by the sensors have to be analyzed by rather sophisticated and therefore costly instruments.

Finally, a further drawback of this system is that the threshold beyond which the phenomenon occurs varies considerably according to the type of pump and the plant configuration.

The object of the present invention is therefore to obviate said drawbacks by providing a sensing-measuring device for determining cavitation in dynamic pumps which by directly sensing the phenomenon is not influenced by other factors extraneous to the phenomenon itself and is also able to sense it from the formation of the initial gas bubbles, i.e. at incipient cavitation, and which further has no need for the constant presence of an operator or the use of sophisticated and costly instrumentation, and which by continuously analyzing the phenomenon enables complete information to be obtained in relation to its progress with time.

This is attained substantially in that the amount of light reflected by the rotating blades of a dynamic pump depends on a large number of factors, but in all cases undergoes significant variation when the cavitation phenomenon is present. Indeed, from experimental tests it has been found that as early as the formation of the initial gas bubbles on the leading edge of the blades, i.e. at incipient cavitation, there is an appreciable change in reflected light from that obtained when bubbles are absent, this change being already sufficient for sensing by a sensor, and increasing in proportion to the extent of the phenomenon.

It is therefore necessary only to arrange a sensor in proximity to the suction nozzle leading to the blades of the first stage of the dynamic pump, this sensor consisting of a light emitter and a light sensor which are inclined at an angle to each other so as to perfectly centre on the leading edge of the blades and thus be able to sense the cavitation phenomenon from its commencement. In this manner, the light emitted by the rotating blades energizes the optical sensor, which generates an electrical signal proportional to the radiation incident on it. When cavitation begins, said radiation incident on the optical sensor undergoes a light change which is converted into a corresponding variation in said electrical signal, the value of which, suitable amplified by usual means, can be used to generate an alarm indicative of the presence of cavitation. Again, continuous measurement of the electrical signal produced by the sensor, this being proportional to the phenomenon, enables complete information to be obtained regarding the progress of the phenomenon with time.

Thus, the sensing-measuring device for the continuous determination of cavitation in dynamic pumps comprising a series of rotating blades and a suction nozzle, is characterised according to the present invention by consisting of an optical probe mounted in proximity to said suction nozzle of the pump, said probe comprising a light emitter and an optical sensor which are positioned inclined at an angle to each other in such a manner as to perfectly centre on the leading edge of said blades.

According to a preferred embodiment of the present invention, said optical probe, comprising a light emitter and an optical sensor, is housed in a hermetically sealed steel tube provided at its active end with a transparent window, said tube being inserted into a suitable hole provided in said pump suction nozzle and fixed therein in such a manner as not to protrude into the in-drawn fluid in order not to disturb the fluid flow at the pump inlet.

The invention is described hereinafter with reference to the accompanying drawing which illustrates a preferred embodiment thereof by way of non-limiting example only, in that technical and constructional modifications can be made thereto but without leaving the scope of the present invention.

Thus for example, the sensor of the invention can be used to analyze the cavitation on a specific blade of the pump; for this purpose, knowing the pump rotational speed, it is necessary only to cause the light emitter to emit light pulses synchronized with said rotational speed.

In said drawing, the FIGURE represents a partly sectional partial view of a sensing-measuring device according to the invention applied to a centrifugal pump.

In the FIGURE the reference numeral 1 indicates the pump impeller, which is provided with blades 2, 3, 4, 5, its shaft 6 being rotated in the direction of the arrow 7. The reference numeral 8 indicates the diffuser channel provided in the pump casing 9, and finally 10 indicates the impeller suction nozzle. In said nozzle 10 there is provided a hole 11 in which there is fixed a hermetically sealed steel tube 12 provided with a transparent window 13 through which there operates an optical probe housed in said tube 12 and powered via the connecter 14 which is also used to withdraw the electrical signal generated by said probe. Said tube 12 is fixed in said hole 11 in such a manner as not to protrude into said suction nozzle 10 (see the figure) in order not to create obstacles and therefore disturbances to the fluid to be drawn in.

Said optical probe consists of a light emitter 15 positioned to coverge its light beam 16 onto the leading edge (5' in the figure) of the blades 2-5 of the impeller 1, and an optical sensor 17 arranged to produce an electrical signal proportional to the extent of the light beam 18 reflected by the blades, said sensor and said emitter being positioned inclined at an angle to each other in such a manner as to centre on the same blade region.

We claim:

1. A sensing-measuring device for the continuous determination of cavitation in dynamic pumps comprising a series of blades and a suction nozzle, characterised by consisting of an optical probe mounted in proximity to said suction nozzle of the pump, said probe comprising a light emitter and an optical sensor which are positioned inclined at an angle to each other in such a manner as to perfectly centre on the leading edge of said blades.

2. A sensing-measuring device for the continuous determination of cavitation as claimed in claim 1, characterised in that said optical probe, comprising a light emitter and an optical sensor, is housed in a hermetically sealed steel tube provided at its active end with a transparent window, said tube being inserted into a suitable hole provided in said pump suction nozzle and fixed therein such a manner as not to protrude into the in-drawn fluid.

* * * * *